United States Patent
O'Kane

(10) Patent No.: US 7,231,840 B1
(45) Date of Patent: Jun. 19, 2007

(54) LIQUID THICKNESS MEASURING AND SAMPLING DEVICE

(75) Inventor: Robert C. O'Kane, Albertson, NY (US)

(73) Assignee: Consolidated Edison Company of New York, Inc., New York, NY (US)

( * ) Notice: Subject to any disclaimer, the term of this patent is extended or adjusted under 35 U.S.C. 154(b) by 0 days.

(21) Appl. No.: 10/834,811

(22) Filed: Apr. 28, 2004

Related U.S. Application Data

(63) Continuation of application No. 10/124,638, filed on Apr. 16, 2002, now abandoned.

(51) Int. Cl.
*G01N 1/12* (2006.01)

(52) U.S. Cl. .................. 73/864.67; 73/864.63

(58) Field of Classification Search .............................. 73/864.66–864.67, 864.63
See application file for complete search history.

(56) References Cited

U.S. PATENT DOCUMENTS

| | | | |
|---|---|---|---|
| 1,544,206 A | 6/1925 | Beard | |
| 1,606,104 A | 11/1926 | Schlueter et al. | |
| 2,137,128 A | 11/1938 | Blake | |
| 2,174,100 A * | 9/1939 | Walker | 73/864.65 |
| 2,255,369 A * | 9/1941 | Spaeth | 73/863.85 |
| 3,097,532 A * | 7/1963 | Brown et al. | 73/864.65 |
| 3,222,928 A | 12/1965 | Walker | |
| 3,390,463 A | 7/1968 | Hirsch | |
| 3,442,017 A | 5/1969 | Frenkel | |
| 3,489,012 A | 1/1970 | Niskin | |
| 3,594,906 A | 7/1971 | Kerfoot | |
| 3,673,850 A | 7/1972 | Burrus | |
| 4,184,363 A | 1/1980 | Vassilev et al. | |
| 4,346,519 A | 8/1982 | Milo | |
| 4,583,293 A | 4/1986 | Smith | |
| 4,760,747 A | 8/1988 | Fackler | |
| 4,960,002 A | 10/1990 | Isotalo | |
| 5,072,625 A | 12/1991 | Anderson | |
| 5,094,113 A | 3/1992 | Wood | |

FOREIGN PATENT DOCUMENTS

JP      56011301 A2    4/1981

* cited by examiner

*Primary Examiner*—Hezron Williams
*Assistant Examiner*—Nashmiya Fayyaz
(74) *Attorney, Agent, or Firm*—Morgan & Finnegan, L.L.P.

(57) ABSTRACT

A method of and an apparatus for measuring the thickness of one liquid layer overlying another liquid layer. The liquid thickness measuring device consists of a tubular casing, constructed of a transparent material, a resiliently biased valve member and a retaining member. The resiliently biased valve member is pivotally movable between open and closed positions to alternatively allow liquid to be sampled to enter the casing when in the open position and to seal the liquid sample when in the closed position. In operation, with the valve member disengaged from the bottom of the tubular casing, the measuring device is slowly lowered into the enclosed device. As a result, the liquid present in the enclosed structure is conductible through the opening of the tubular casing, to seek its level in the tubular member. The retaining member, which engages and holds the valve in an open position, is then released and the valve is allowed to move to the closed position. Accordingly, an accurate assessment can be made of the thickness of stratified liquid layers in the enclosed structure by measuring the thickness or height of the layers in the tubular casing.

44 Claims, 4 Drawing Sheets

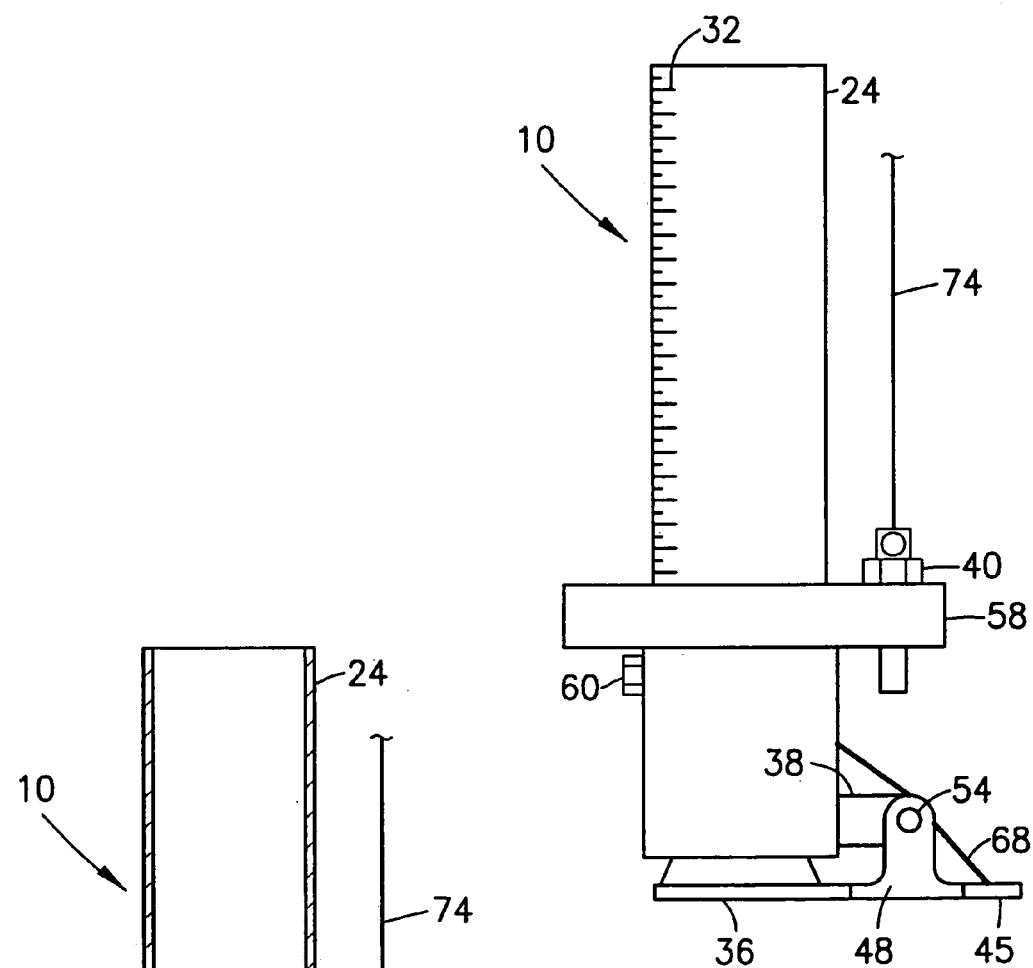
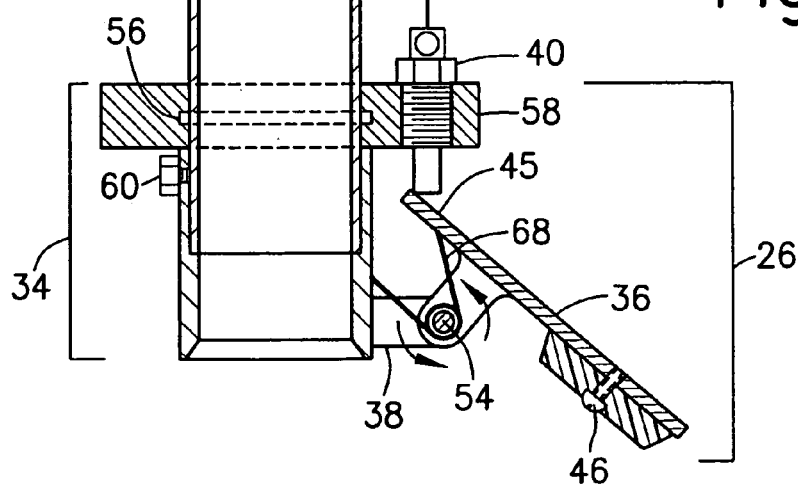
Fig. 3
Fig. 2

LIQUID THICKNESS MEASURING AND SAMPLING DEVICE

This is continuation of application Ser. No. 10/124,638, filed Apr. 16, 2002, now abandoned.

FIELD OF THE INVENTION

The field of this invention relates to liquid sampling and measuring devices. More particularly, the invention pertains to measuring devices which can be used to determine the thickness of various strata of immiscible fluids.

BACKGROUND OF THE INVENTION

The use of devices for sampling and measuring contained liquids is well recognized by those skilled in the art. Typically, such devices assist in determining the quantity, thickness, and relative location of various immiscible liquids which may be present within a storage tank, underground well, drum or similar container means. The devices are also used to obtain information relating to interior tank conditions, such as the possible presence of contaminants. Additionally, some of the devices permit samples of the stored fluid to be taken from the tank or container means for testing purposes.

The vast majority of prior art liquid sampling and measuring devices consist of a tubular casing, a valve, and an actuating mechanism which opens or closes the valve. The valve is usually located at the lowermost end of the tubular casing and controls whether or not liquid is permitted to flow into the tubular casing. For example, if the valve is in the open position, then liquid is permitted to flow into the tubular casing, and if the valve is in the closed position, then the opening is blocked and liquid is prohibited from entering or leaving the tubular casing. Essentially, the basic overall structures of the prior art devices are identical. However, the prior art devices differ from one another in the type of valve, the valve construction and the actuating mechanism utilized in their construction. For example, a number of the prior art devices consist of an actuating mechanism which functions to open or close the valve when the device is engaged with the bottom of the storage tank. See, e.g., U.S. Pat. No. 4,760,747 issued to Fackler and U.S. Pat. No. 4,346,519 issued to Milo. Additional prior art measuring devices include a sealing device which is comprised of a sealing plug, a sealing ring and a series of openings. A threaded sleeve engages the lower end of the tubular member and a sealing plate is attached within the outer or free end of the sleeve. During operation, the tubular member is rotated relative to the sleeve in order to cause the sealing member to be engaged or disengaged from the seat. See, U.S. Pat. No. 4,583,293 issued to Smith. The majority of prior art devices include valves and actuating mechanisms that are complex in design and function and incorporate multiple parts and complex mechanisms. The maintenance of those devices, such as decontamination and repair of the complex valving assemblies, is tedious, time-consuming and often difficult.

The majority of the known sampling and measuring devices is employed to obtain a liquid sample of the contents of a reservoir or underground tank and to determine if any contaminants exist. Those devices can also be employed to ascertain the thickness of immiscible fluid levels in the underground tank or container.

In addition to the sampling devices described supra, alternative devices exist in the prior art to determine the thickness of one liquid layer overlying another. Some of these employ sophisticated components such as electronic sensors to detect the interface between the two immiscible fluids and to determine the thickness of the immiscible layers. See, e.g., U.S. Pat. No. 4,184,363 issued to Vassilev et al. One drawback of the relatively sophisticated sampling devices is that they are costly. Some of the devices also can be time consuming operate. Additionally, several of such devices, including most of the electronic phase metering devices are prone to error when heavy contamination is present, and do not allow a sample of the liquid to be taken.

Accordingly, the need exists for a liquid sampling and measuring device that can provide a quick and accurate measurement of the thickness of various strata of immiscible fluids and yet is simple in design and construction and is straightforward to operate when taking samples.

SUMMARY OF THE INVENTION

The liquid thickness measuring and sampling device and method of the present invention allows the thickness of various strata of immiscible fluids found in an enclosed container to be determined. In a preferred embodiment, the invention includes an elongated tubular casing, a valve assembly, a valve retaining member, and actuating means for operating the retaining member to enable a valve to trap and seal a sample within the cavity. The valve assembly includes two parts, a resiliently biased valve member and a valve body. The valve assembly is carried at the lower end of the casing and can be opened to admit liquid into the casing when the device is lowered into a pool of liquid and then closed to seal the opening and trap the sample within the casing. A retaining member engages and holds the valve member in an open position until it is disengaged from the valve member to allow it to move from the open position to the closed position.

DESCRIPTION OF THE FIGURES

For a more complete understanding of the invention, together with its modes of operation and advantages, reference should be made to the following detailed description of preferred embodiments and to the accompanying drawings.

FIG. 2 is a detailed side elevation, cross-sectional view of the device, illustrating the valve assembly in the open position;

FIG. 3 is a detailed side elevation view of the device, illustrating the valve assembly in the closed position;

DETAILED DESCRIPTION OF THE PREFERRED EMBODIMENT

Figure 1:
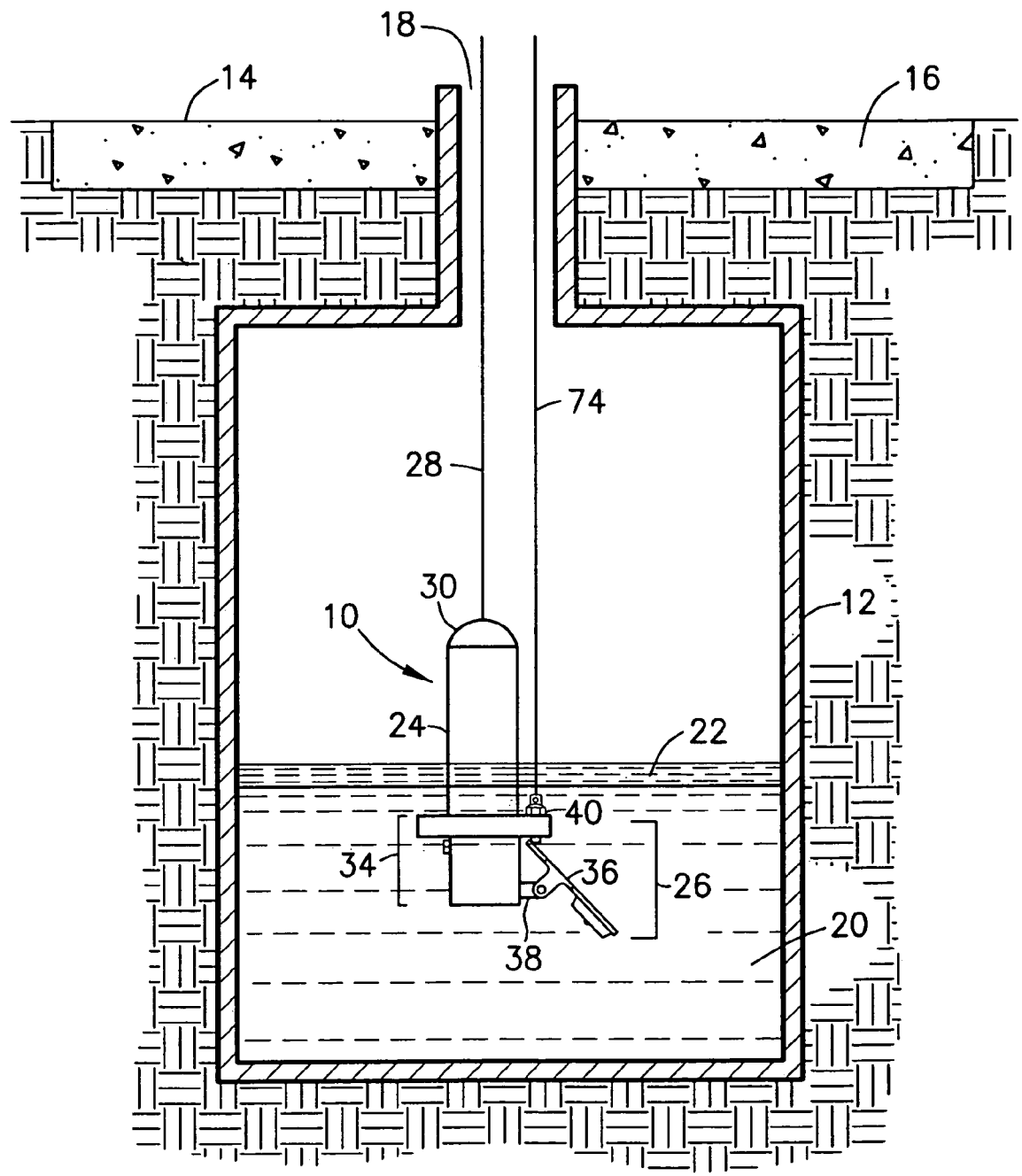
FIG. 1 is a side elevation view of the preferred embodiment of the liquid thickness measuring device, illustrating its use within an underground liquid storage tank.

FIG. 1 illustrates a liquid sampling and measuring device 10, in use within an enclosed structure 12, such as a storage tank, manhole or vault, typically installed below the ground surface 14. In FIG. 1, the enclosed structure 12 is depicted as a vault having a concrete slab 16 over the structure for safety purposes in accordance with national and local safety codes. Frequently, such structures are used to house utility equipment such as electrical, steam or telephone conduits, junctions, valves, etc. In other cases, the structure can be a storage tank for liquids.

The enclosed structure 12 may include various liquids and/or undesired contaminants that are immiscible, and thus, it is necessary or advantageous to have some means for determining the existence of fluids or contaminants that are stratified within the structure. For example, in FIG. 1, the immiscible fluids are water 20 and oil 22. The thickness of the oil layer 22 can easily be determined by utilizing the liquid sampling and measuring device 10 of the invention. To that end, the liquid sampling and measuring device is inserted and lowered into the enclosed structure 12 via a manhole, handhole, or other opening 18. It is then manipulated to extract a sample of the stratified liquid of which the vertical extent of the sample is a direct measure of the thickness of the stratified fluid layer within the structure 12.

As depicted in FIG. 1, the liquid sampling and measuring device 10 comprises a tubular casing 24, a valve assembly 26, which includes a valve member 36 and a valve body 34, a lowering support 28, a spring-loaded retaining member in the form of a plunger 40, and actuating means 74 attached to the retaining member. Typical supports include rigid poles, rods, sticks, strings, telescoping devices, lanyards and motorized devices. The support 28 can be permanently or removably attached to the measuring device 10 at a connection fixture 30 attached at the top of the measuring device 10. In operation, the valve member 36 is locked in an open position, as illustrated in FIG. 1, by the plunger 40, while the measuring device 10 is slowly lowered into the enclosed structure and through the liquid mixture. With the valve member 36 in the open position, the device easily passes through the immiscible layers without restriction.

The construction of the measuring device is better seen in FIGS. 2 and 3. As illustrated, the casing 24 is a hollow cylinder constructed of a transparent material, preferably a plastic such as polyethylene or polycarbonate. However, the most suitable material for the casing is usually dictated by the corrosive action of the liquids being sampled or measured. Also, the casing 24 can take other cross-sectional forms and need not be circular. The casing 24 is open at the bottom end and either open or vented to the atmosphere at the top end. A measuring scale 32 (FIG. 3) may be inscribed or applied on either the exterior or interior sidewalls of the casing 24, and preferably extends the entire length of the casing.

A resiliently biased valve assembly 26 is located at the bottom end of the tubular casing. The valve assembly includes a valve body 34 and a valve member 36. The valve body 34 constitutes an extension of the casing and includes a mounting bracket 38 for supporting the valve member 36 and a collar 58 for supporting the spring-loaded retaining member 40. In the preferred embodiment, the top end of the valve body 34 is dimensioned to receive the cylindrical casing 24, which is secured to the valve body 34 via a set screw 60 and sealed by an O-ring 56. Of course, in lieu of a set screw 60, any of a number of conventional securing devices may also be used. Alternatively, the mating portions of the valve body and casing may be threaded and secured together by the threads. It shall be understood that any technique known by those skilled in the art may be used to effectively attach the valve body 34 and the tubular casing 24.

The resiliently biased valve member 36 is attached to the valve body 34 on the mounting bracket 38. The valve member 36 is affixed to the mounting bracket 38 so that it is free to pivot transversely to the axis of the tubing, between open and closed valve positions. The valve member is attached to the mounting bracket via a hinge pin 54. A torsion spring 68 surrounds the hinge pin and provides the resilient biasing force toward the closed position for the valve member. The force exerted by the spring should be strong enough to seal the opening at the bottom of the tubular casing against leakage of the sample. Likewise, the hinge should have sufficient precision to guide the valve member into sealing engagement with the bottom opening of the casing.

As illustrated in FIG. 2, the valve member 36 is held in the open, i.e. "locked," position by the retaining member, which is a spring-loaded plunger 40 in the illustrative embodiment. The plunger 40 is controllably movable from a valve member-engaging position to a valve member-disengaging position, by triggering the actuating device 74. With the valve member locked in the open position, liquid is allowed to enter the casing as it is passed through the liquid surface. When the plunger 40 disengages the valve member, it moves to the closed position under the influence of the resilient biasing force, thus sealing the bottom aperture of the tubular casing.

FIG. 3 illustrates the valve member in its closed position. Typical actuating devices 74 include, but are not limited to, rods, strings, telescoping devices and lanyards. In one embodiment, the activating device is manually operable. Alternatively, the actuating device may be controlled by a motorized system. In the preferred embodiment, the plunger 40 is a stubby pull-ring nonlocking nose, Item No. PRSN250, manufactured by M.J. Vail Company, Inc., U.S.A.

Figure 4A:
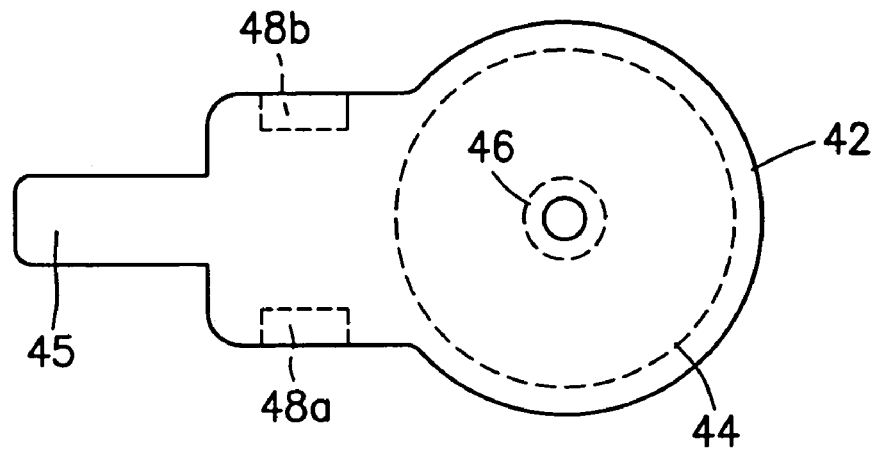
FIG. 4a is a bottom plan view of the preferred embodiment.
Figure 4B:
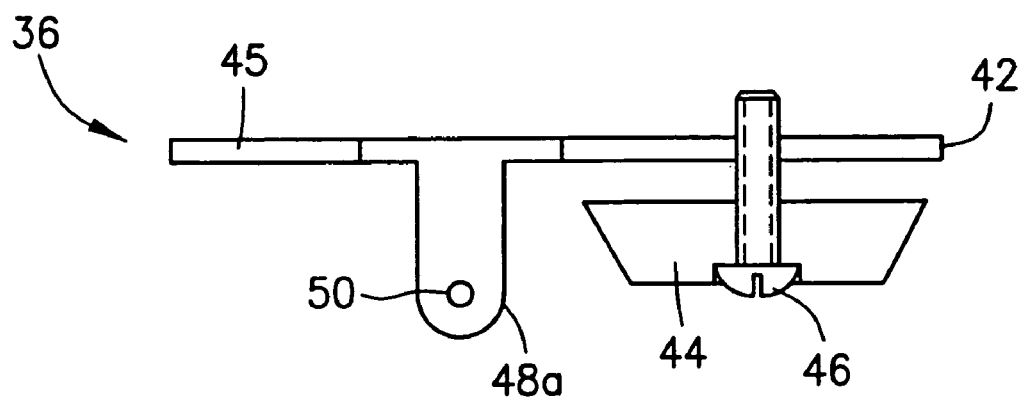
FIG. 4b is a detailed side elevation view of the valve member.
Figures 5A, 5B:
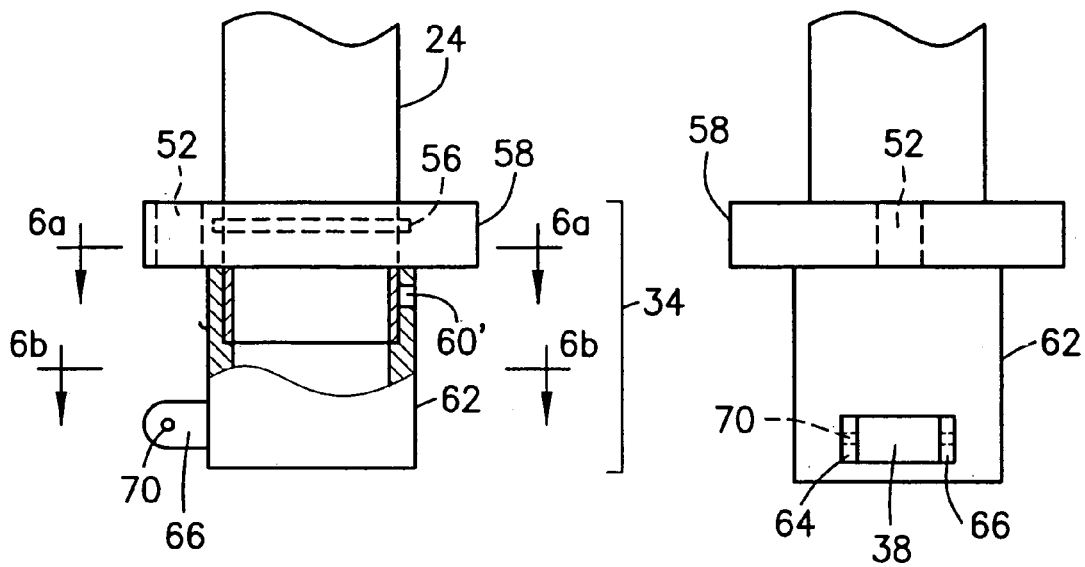
FIG. 5a is a side elevation, cross-sectional view of the valve body.
FIG. 5b is a front elevation view of the valve body.

As seen in FIGS. 4a and 4b, the valve member is constructed so as to securely and positively plug the aperture of the tubular casing when closed. To that end, the valve member 36 includes a circular base 42 and a rubber stopper 44 attached to the circular base by a suitable screw fastener 46. This allows the rubber stopper 44 to be easily removed for replacement, maintenance or repair (see FIG. 4b). Of course, other means, such as adhesives or resilient clamping arms (not shown) may be employed to affix the circular base 42 and the rubber stopper 44. However, it is preferable that the stopper 44 can be easily removed and reattached to the circular base 42. The base also includes a rear extension 45 which, as will be explained, provides a surface that can be engaged by the plunger 40 to lock the valve member in the open position. The valve member 36 further comprises a hinge mount 48 to attach the valve member 36 to the valve body 34. The hinge mount 48 includes two projections 48a, 48b extending generally perpendicularly from the valve member's underside (stopper side). The projections have a hole 50 at the valve member 36 pivot point for receiving a hinge pin 54 that extends through the projections and bores, into the mounting bracket 38 of the valve body.

The construction of the valve body is better seen in FIGS. 5a, 5b, 6a and 6b. As illustrated, in FIG. 5b, the valve body 34 is divided into two parts; a collar 58 at the top and a bottom cylindrical section 62. The collar 58 provides a spring plunger mounting aperture 52 and the lower section includes the mounting bracket 38. Specifically, the collar is dimensioned to support the plunger against the resilient force of the torsion spring when the valve member is "locked" in the open position. The position of the spring plunger 40 relative to the rear extension 45 of the valve member 36 determines the angle of the valve member 36 relative to the tubular casing 24 when it is "locked" open. In order to vary the "locked" open position of the valve member, the position of the spring plunger may be altered or the design of the valve member, specifically the rear extension 45 can be modified. The position of the spring plunger 40 can be modified by altering the dimensions of the collar 58 or by allowing the collar to be movable in the vertical direction. The movable collar 58 allows the valve member 36 to be locked open to different degrees. In order to facilitate movement of the collar in the vertical direction, the set screw 60' should be countersunk.

Figures 6A, 6B:
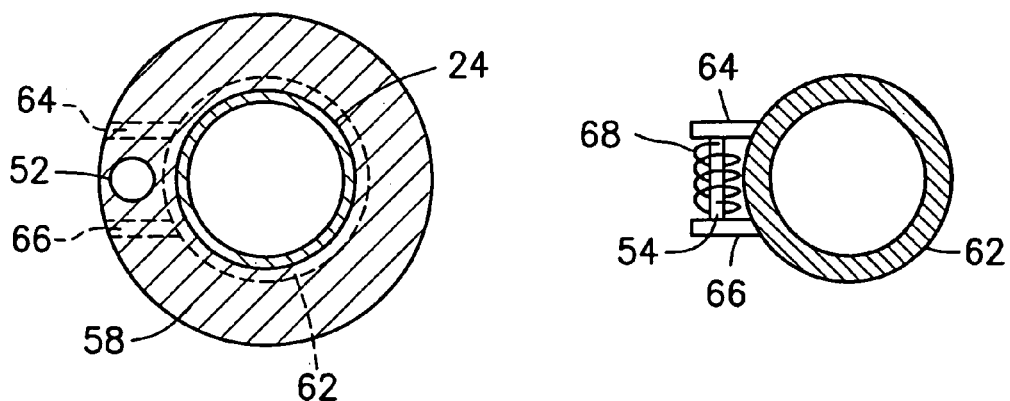
FIGS. 6a and 6b are cross-sectional views along the width of the valve body taken along lines 6a–6a and 6b–6b, in FIG. 5A, and illustrating the spring plunger and the valve member mounting areas, respectively.

Referring to FIG. 6b, the mounting bracket 38 comprises two parallel-arms 64, 66 which extend perpendicularly from the bottom section of valve body 62. These may be either mechanically affixed to the valve body or cast elements as illustrated. The two projections each have a hole 70 to receive a hinge pin 54, upon which the valve member can pivot. The coiled torsion spring 68, is positioned between the arms 64, 66. In the preferred embodiment, a heavy torsion spring with 10.5 coils is used.

Referring to FIG. 6a, the diameter of the aperture 52 is dimensioned to receive a spring plunger of appropriate size. In the preferred embodiment, the hole is a threaded ¼"×20 TPI bore.

To use the measuring device, the resiliently biased valve member 36 is pivoted against the force of the spring 68 toward the spring plunger 40. The plunger is manually retracted upwardly as the valve member passes over the bottom of the plunger. The plunger is then allowed to return to its normal (downwardly biased) position, whereby it engages the extension 45. This locks the valve member 36 in the open position. Thereafter, the measuring device is slowly lowered into the liquids as illustrated in FIG. 1, and passes through any layers of immiscible fluids that may exist at the top surface, such as an oil layer suspended at the top of a water layer. As a result, the liquids seek their own level inside the casing. This occurs within a matter of a second or two. After a proper sample has been taken, the actuating device which is attached to the spring plunger, such as a lanyard is pulled, thereby retracting the plunger and disengaging the valve member. Thus, the valve will automatically close under the bias of the spring. Accordingly, the integrity of the sample is preserved as it is brought to the surface.

As the device is raised out of the enclosed structure, the immiscible fluids, e.g., the oil and water trapped in the tubular casing will separate, with the less dense oil layer floating on the water layer. As the measuring device is removed from the pool of liquids, it brings with it a profile sample of the oil and water layers, the thickness of the oil layer within said tubular casing being the same thickness as the oil layer in the body of liquids being sampled. Accordingly, an accurate assessment can be made of the thickness of the original oil layer by measuring the vertical thickness of the floating oil in the tubular casing. This can be accomplished by measuring it with a ruler or by utilizing the measurement markings located on the tubular casing. This thickness measurement is then used to calculate the total volume of oil within a structure of known geometry.

The valve assembly of the claimed device is simple in design and consists of few parts. Thus, it is easily fabricated, repaired and replaced. In use, the measuring device may contact hydrocarbons and should be regularly maintained and decontaminated. The simplicity of its design renders such maintenance easy to perform.

While the invention has been described in terms of the preferred embodiment, this embodiment is illustrative only, and many alternatives and equivalents will readily occur to those skilled in the art, without departing from the spirit or proper scope of the invention as set forth in the appended claims.

What is claimed is:

1. A liquid thickness measuring and sampling device comprising:
   an elongated tubular casing having an opening at a lower end thereof, for admitting into the casing a liquid to be sampled;
   a valve assembly, at the lower end of the tubular casing, comprising a resiliently biased valve member and a valve body mounted to the tubular casing, wherein a bottom end of the valve body defines a valve seat;
   the resiliently biased valve member supported by the valve body at a pivot point for movement between open and closed positions to allow the liquid to be sampled to enter the casing when in the open position and to seal the liquid sample in the casing when in the closed position, wherein the valve member is resiliently biased by a torsion spring situated about the pivot point for rotation of the valve member into the closed position, and further wherein the valve member is pivotally movable about an axis that is in a plane transverse to a vertical axis of the tubular casing;
   a retaining member, attached to the valve body, and engageable with the resiliently biased valve member so as to maintain the valve member in an open position while the device is lowered into the liquid;
   the retaining member being controllably operative to disengage the valve member and allow the valve member to move to the closed position, to thereby trap a sample of liquid within the tubular casing during a withdrawal of the measuring device from the liquid being sampled; and
   wherein the pivot point is located at a lower end of the valve body.

2. The device according to claim 1, wherein the elongated tubular casing is constructed of a transparent material to permit a withdrawn liquid sample to be viewed without discharging the sample from the casing.

3. The device of claim 1, wherein the valve body is removeably mounted at a lower portion of the tubular casing.

4. The device according to claim 3, wherein the valve body includes a set screw to secure the tubular casing therein.

5. The device according to claim 4, wherein the set screw is countersunk.

6. The device according to claim 1, wherein the valve member is hinged to the valve body.

7. The device according to claim 1, wherein a top end of the valve body is dimensioned to receive the tubular casing therein.

8. The device according to claim 1, wherein the resiliently biased valve member comprises a metal base and a compliant stopper mounted to the metal base.

9. The device according to claim 1, wherein the retaining member is a spring-biased plunger directly engageable with the valve member.

10. The device according to claim 1, further comprising an actuator element attached to the retaining member, and accessible to a user when the device is positioned to sample a liquid to allow the retaining member to disengage, the resiliently biased valve member for movement to the closed position.

11. The device according to claim 10, wherein the actuator is selected from the group consisting of lanyards, strings, and rods.

12. The device according to claim 1, wherein the valve member includes a rear extension which provides a surface that is engaged by the retaining member to maintain the valve member in the open position.

13. The device according to claim 2, further comprising a graduated scale on the surface of the tubular casing for determining the depth of a liquid layer within the tubular casing.

14. The device according to claim 1, further comprising means for lowering the device into an enclosed structure.

15. The device according to claim 14, wherein the lowering device is a rigid pole.

16. The device according to claim 14, wherein the lowering device is a telescoping pole.

17. The device according to claim 1, wherein the retaining member is attached to the valve body upward from the pivot point, and is engageable with a rear extension of the resiliently biased valve member.

18. A liquid thickness measuring and sampling device comprising:
    an elongated tubular casing for holding a liquid to be sampled, the casing having a lower end which is open and an upper end which is vented to the atmosphere to allow the liquid to enter the casing from the lower end thereof when the casing is lowered into a liquid contained in an enclosed structure for sampling immiscible liquid layers in the enclosed structure;
    a valve assembly, at the lower end of the tubular casing, comprising a resiliently biased valve member and a valve body mounted to the tubular casing, the valve body having a collar and a tubular section;
    the resiliently biased valve member being supported by the valve body at a pivot point for movement between open and closed positions to allow the liquid to be sampled to enter the casing when in the open position and to seal the liquid sample in the casing when in the closed position, wherein the valve member is resiliently biased by a torsion spring situated about the pivot point for rotation of the valve member into the closed position, and further wherein the valve member is pivotally movable about an axis that is in a plane transverse to a vertical axis of the tubular casing;
    a retaining member, supported on the collar of the valve body, and engageable with the resiliently biased valve member so as to maintain the valve member in an open position while the device is lowered into the liquid;
    the retaining member being controllably operative to disengage the valve member and allow the valve member to move to the closed position to thereby trap the sample of liquid within the tubular casing during a withdrawal of the measuring device from the liquid being sampled; and
    wherein the pivot point is located at a lower end of the valve body.

19. The device according to claim 18, further comprising a hinge pin for pivotally mounting the resiliently biased valve member to the valve body.

20. The device according to claim 19, wherein the torsion spring is located by the hinge pin and provides a resilient biasing force acting between the valve member and the valve body to close the valve member.

21. The device according to claim 18, wherein the collar is movable in the vertical direction.

22. The device according to claim 18, wherein the retaining member is attached to the valve body upward from the pivot point, and is engageable with a rear extension of the resiliently biased valve member.

23. A liquid thickness measuring and sampling device comprising:
    an elongated tubular casing having an opening at a lower end thereof, for admitting into the casing a liquid to be sampled;
    a valve assembly, at the lower end of the tubular casing, comprising a resiliently biased valve member and a valve body mounted to the tubular casing, wherein a bottom end of the valve body defines a valve seat;
    the resiliently biased valve member supported by the valve body at a pivot point for movement between open and closed positions to allow the liquid to be sampled to enter the casing when in the open position and to seal the liquid sample in the casing when in the closed position, wherein the valve member is resiliently biased by a torsion spring situated about the pivot point for rotation of the valve member into the closed position, and further wherein the valve member is pivotally movable about an axis that is in a plane transverse to a vertical axis of the tubular casing;
    a retaining member, attached to the valve body, and engageable with the resiliently biased valve member so as to maintain the valve member in an open position while the device is lowered into the liquid;
    the retaining member being controllably operative to disengage the valve member and allow the valve member to move to the closed position, to thereby trap a sample of liquid within the tubular casing during a withdrawal of the measuring device from the liquid being sampled; and
    wherein the retaining member is attached to the valve body upward from the pivot point, and is engageable with a rear extension of the resiliently biased valve member.

24. The device according to claim 23, wherein the elongated tubular casing is constructed of a transparent material to permit a withdrawn liquid sample to be viewed without discharging the sample from the casing.

25. The device according to claim 23, wherein a top end of the valve body is dimensioned to receive the tubular casing therein.

26. The device according to claim 23, wherein the valve member is hinged to the valve body.

27. The device according to claim 23, wherein the resiliently biased valve member comprises a metal base and a compliant stopper mounted to the metal base.

28. The device according to claim 23, wherein the retaining member is a spring-biased plunger directly engageable with the valve member.

29. The device according to claim 23, further comprising an actuator element attached to the retaining member, and accessible to a user when the device is positioned to sample a liquid to allow the retaining member to disengage, the resiliently biased valve member for movement to the closed position.

30. The device according to claim 29, wherein the actuator is selected from the group consisting of lanyards, strings, and rods.

31. The device according to claim 23, wherein the valve member includes a rear extension which provides a surface that is engaged by the retaining member to maintain the valve member in the open position.

32. The device according to claim 24, further comprising a graduated scale on the surface of the tubular casing for determining the depth of a liquid layer within the tubular casing.

33. The device according to claim 23, further comprising means for lowering the device into an enclosed structure.

34. The device according to claim 33, wherein the lowering device is a rigid pole.

35. The device according to claim 33, wherein the lowering device is a telescoping pole.

36. The device of claim 23, wherein the valve body is removeably mounted at a lower portion of the tubular casing.

37. The device of claim 23, wherein the pivot point is located at a lower end of the valve body.

38. The device according to claim 36, wherein the valve body includes a set screw to secure the tubular casing therein.

39. The device according to claim 38, wherein the set screw is countersunk.

40. A liquid thickness measuring and sampling device comprising:
    an elongated tubular casing for holding a liquid to be sampled, the casing having a lower end which is open and an upper end which is vented to the atmosphere to allow the liquid to enter the casing from the lower end thereof when the casing is lowered into a liquid contained in an enclosed structure for sampling immiscible liquid layers in the enclosed structure;
    a valve assembly, at the lower end of the tubular casing, comprising a resiliently biased valve member and a valve body mounted to the tubular casing, the valve body having a collar and a tubular section;
    the resiliently biased valve member being supported by the valve body at a pivot point for movement between open and closed positions to allow the liquid to be sampled to enter the casing when in the open position and to seal the liquid sample in the casing when in the closed position, wherein the valve member is resiliently biased by a torsion spring situated about the pivot point for rotation of the valve member into the closed position, and further wherein the valve member is pivotally movable about an axis that is in a plane transverse to a vertical axis of the tubular casing;
    a retaining member, supported on the collar of the valve body, and engageable with the resiliently biased valve member so as to maintain the valve member in an open position while the device is lowered into the liquid;
    the retaining member being controllably operative to disengage the valve member and allow the valve member to move to the closed position to thereby trap the sample of liquid within the tubular casing during a withdrawal of the measuring device from the liquid being sampled; and
    wherein the retaining member is attached to the valve body upward from the pivot point, and is engageable with a rear extension of the resiliently biased valve member.

41. The device according to claim 40, further comprising a hinge pin for pivotally mounting the resiliently biased valve member to the valve body.

42. The device according to claim 41, wherein the torsion spring is located by the hinge pin and provides a resilient biasing force acting between the valve member and the valve body to close the valve member.

43. The device according to claim 40, wherein the collar is movable in the vertical direction.

44. The device of claim 40, wherein the pivot point is located at a lower end of the valve body.

* * * * *